(12) United States Patent
Green et al.

(10) Patent No.: US 8,975,578 B2
(45) Date of Patent: Mar. 10, 2015

(54) ASYMMETRIC FIELD ION MOBILITY IN A LINEAR GEOMETRY ION TRAP

(75) Inventors: Martin Raymond Green, Bowdon (GB); Kevin Giles, Stockport (GB); David J. Langridge, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 13/881,840

(22) PCT Filed: Oct. 26, 2011

(86) PCT No.: PCT/GB2011/052085
§ 371 (c)(1),
(2), (4) Date: Jul. 25, 2013

(87) PCT Pub. No.: WO2012/056239
PCT Pub. Date: May 3, 2012

(65) Prior Publication Data
US 2013/0306858 A1    Nov. 21, 2013

(30) Foreign Application Priority Data

Oct. 27, 2010   (GB) .................................. 1018184.0

(51) Int. Cl.
*H01J 49/04*       (2006.01)
*G01N 27/62*       (2006.01)
(Continued)

(52) U.S. Cl.
CPC .............. *H01J 49/04* (2013.01); *G01N 27/622* (2013.01); *H01J 49/0031* (2013.01); *H01J 49/36* (2013.01)
USPC ........... 250/283; 250/281; 250/282; 250/288; 250/290; 250/292

(58) Field of Classification Search
USPC .................. 250/281, 282, 283, 288, 290, 292
See application file for complete search history.

(56) References Cited

U.S. PATENT DOCUMENTS

| 7,034,286 | B2 | 4/2006 | Guevremont et al. |
| 7,205,538 | B2 * | 4/2007 | Bateman et al. .............. 250/292 |
| 7,285,774 | B2 | 10/2007 | Guevremont |

(Continued)

FOREIGN PATENT DOCUMENTS

| GB | 2423866 | 9/2006 |
| GB | 2455377 | 6/2009 |

(Continued)

OTHER PUBLICATIONS

Okamoto, "*FAIMS-MS (High Field Asymmetric Waveform Ion Mobility Spectrometry—Mass Spectrometry)*", Japan Society for Bioscience, Biotechnology, and Agrochemistry, vol. 46, No. 6, pp. 376-377, 2008.

(Continued)

*Primary Examiner* — Phillip A Johnston
*Assistant Examiner* — Hsien Tsai
(74) *Attorney, Agent, or Firm* — Diederiks & Whitelaw, PLC

(57) ABSTRACT

A linear ion trap is disclosed wherein an asymmetric voltage waveform is applied to electrodes forming the ion trap which causes ions to become radially separated according to their differential ion mobility. An axial potential barrier is arranged at the exit of the ion trap such that ions having a first differential ion mobility and a first radial displacement are retained axially within the ion trap but ions having a second differential ion mobility and a second radial displacement are ejected axially from the ion trap.

17 Claims, 15 Drawing Sheets

(51) Int. Cl.
  *H01J 49/00* (2006.01)
  *H01J 49/36* (2006.01)

(56) References Cited

U.S. PATENT DOCUMENTS

| | | | |
|---|---|---|---|
| 8,426,803 | B2 | 4/2013 | Green et al. |
| 8,440,967 | B2 | 5/2013 | Giles |
| 8,440,968 | B2 | 5/2013 | Giles |
| 2002/0134932 | A1 | 9/2002 | Guevremont et al. |
| 2004/0046124 | A1 | 3/2004 | Derrick et al. |
| 2009/0057546 | A1* | 3/2009 | Giles .......................... 250/282 |
| 2009/0173880 | A1* | 7/2009 | Bateman et al. ............. 250/292 |
| 2009/0314935 | A1* | 12/2009 | Hoyes ........................... 250/283 |

FOREIGN PATENT DOCUMENTS

| | | |
|---|---|---|
| WO | 2004030129 | 4/2004 |
| WO | 2006059123 | 6/2006 |
| WO | 2009007739 | 1/2009 |

OTHER PUBLICATIONS

Purves et al, "*Electrospray Ionization High-Field Asymmetric Waveform Ion Mobility Spectrometry—Mass Spectrometry*", Analytical Chemistry, vol. 71, No. 13, pp. 2346-2357, 1999.

Sugai, "*Learning Mass Spectrometry from Basics/ Origin of Mass Spectrometry, Chapter 6, Vapor-Phase Mobility*", Journal of the Mass Spectrometry Society of Japan, vol. 58, No. 2, pp. 47-73, 2010.

Buryalcov et al., "*A New Method of Separation of Multi-Atomic Ions by Mobility at Atmospheric Pressure Using a High-Frequency Amplitude-Asymmetric Strong Electric Field*" International Journal of Mass Spectrometry and Ion Processes, vol. 28, pp. 143-148, 1993.

Guevremont et al., "*Comparison of Experimental and Calculated Peak Shapes of Three Cylindrical Geometry FAIMS Prototypes of Differing Electrode Diameters*" American Society for Mass Spectrometry, vol. 16, pp. 349-362, 2005.

Prasad et al., "*Simulation of Ion Motion in FAImS Through Combined Use of SIMION and Modified SDS*" Analytical Chemistry, vol. 81, pp. 8749-8757, 2009.

\* cited by examiner

ASYMMETRIC FIELD ION MOBILITY IN A LINEAR GEOMETRY ION TRAP

CROSS-REFERENCE TO RELATED APPLICATION

This application represents a National Stage application of PCT/GB2011/052085 entitled "Asymmetric Field Ion Mobility in a Linear Geometry Ion Trap" filed 26 Oct. 2011 which claims priority from and the benefit of U.S. Provisional Patent Application Ser. No. 61/421,387 filed on 9 Dec. 2010 and United Kingdom Patent Application No. 1018184.0 filed on 27 Oct. 2010. The entire contents of these applications are incorporated herein by reference.

BACKGROUND TO THE INVENTION

The present invention relates to the field of mass spectrometry and in particular to a differential ion mobility separator.

The mobility K of an ion in a gas in the presence of an electric field E is essentially independent of the field under conditions where the energy gained from the field by the ion is negligible compared with thermal energies. This condition is met when E/N is low, wherein N is the neutral gas number density. However, as the electric field is increased or the neutral gas number density is decreased, then the mobility of an ion becomes dependent on the ratio of E/N:

$$K\left(\frac{E}{N}\right) = K_0\left[1 + \alpha\left(\frac{E}{N}\right)\right] \quad (1)$$

wherein $K_0$ is the low E/N mobility and $\alpha(E/N)$ is a function representing the field dependence.

A knowledge of the dependence of the mobility of an ion on electric field strength prompted development of a differential ion mobility analyser by Buryakov et al. (International Journal of Mass Spectrometry and Ion Processes, 128 (1993), pp 143-148) which disclosed separating ions according to differences between their low and high field mobilities.

The device disclosed by Buryakov et al. consisted of a pair of parallel plates with a gas flow between them. Ions to be separated were entrained in the gas flow.

Known differential ion mobility analysers operate at atmospheric pressure. At atmospheric pressure the rate of ion diffusion is lower than at reduced pressure and so as the gas pressure is reduced, ion diffusion becomes a significant loss mechanism. Conversely, at atmospheric pressure high voltage RF generators are necessary in order to provide values of E/N which are high enough to access high-field mobility conditions.

In known differential ion mobility devices ions having specific differential ion mobility characteristics may be transmitted sequentially as a result of scanning the operating parameters of the device. Ions which have entered the device, but which are not being transmitted, will be lost. This results in very low duty cycle for transmission of analytes having differing ion mobility characteristics during an analytical scan and hence low overall sensitivity.

It is desired to provide an improved differential ion mobility separator and method of separating ions according to their differential ion mobility.

SUMMARY OF THE INVENTION

According to an aspect of the present invention there is provided a linear ion trap comprising:

a plurality of electrodes;

a device arranged and adapted to apply an asymmetric voltage waveform to one or more of the electrodes so that, in use, ions become radially separated in a first radial direction according to their differential ion mobility; and a device arranged and adapted to form, in use, an axial potential barrier at a position along the length of the linear ion trap so that ions having a first differential ion mobility and a first radial displacement are retained axially within the linear ion trap by the axial potential barrier whereas ions having a second different differential ion mobility and a second different radial displacement emerge axially or are ejected axially from the linear ion trap.

The ion trap preferably further comprises a device arranged and adapted to apply a symmetric RF voltage to one or more of the electrodes so that, in use, ions are confined within the ion trap in a second radial direction by a RF pseudo-potential field.

The term "symmetric RF voltage" should be understood as meaning a RF voltage which is applied to the electrodes and which is not intended to cause ions to become radially separated according to their differential ion mobility. In the context of a planar ion guide a symmetric or sinusoidal RF voltage is preferably applied to electrodes so that adjacent planar electrodes are maintained at opposite phases of the RF voltage. According to less preferred embodiments, in the context of a stacked ring ion trap then adjacent ring electrodes are maintained at opposite phases of the RF voltage. In the context of a multipole rod set arrangement then adjacent rod electrodes are maintained at different phases of the RF voltage and diametrically opposed rod electrodes are maintained at the same phase of the RF voltage.

The term "symmetric RF voltage" should therefore be understood as having the effect of causing ions have a wide range of mass to charge ratios to be confined in a radial direction within the ion trap by an inhomogeneous pseudo-potential field which acts to confine ions radially within the ion trap but which does not cause ions to assume substantially different radial positions in accordance with their differential ion mobility.

The second radial direction is preferably orthogonal to the first radial direction.

The ion trap preferably further comprises a device arranged and adapted to maintain an axial DC potential gradient along at least a portion of the axial length of the linear ion trap in a mode of operation in order to urge at least some ions in a first axial direction along the linear ion trap.

The ion trap preferably further comprises a device arranged and adapted:

(i) to apply one or more transient DC voltages or one or more transient DC voltage waveforms to at least some first electrodes in order to urge at least some ions having a first radial displacement in a first axial direction along the linear ion trap; and/or (ii) to apply one or more transient DC voltages or one or more transient DC voltage waveforms to at least some second electrodes in order to urge at least some ions having a second different radial displacement in a second axial direction along the linear ion trap, the second axial direction being different from the first axial direction.

According to an aspect of the present invention there is provided a linear ion trap comprising:

a plurality of electrodes;

a device arranged and adapted to apply an asymmetric voltage waveform to one or more of the electrodes so that, in use, ions become radially separated in a first radial direction according to their differential ion mobility and wherein in a mode of operation ions are ejected from or emerge from the linear ion trap in the first radial direction according to their differential ion mobility; and a device arranged and adapted to apply a symmetric RF voltage to one or more of the electrodes so that, in use, ions are confined within the ion trap in a second radial direction by a RF pseudo-potential field.

The second radial direction is preferably orthogonal to the first radial direction.

The linear ion trap is preferably operated or maintained at a pressure selected from the group comprising: (i) <100 mbar; (ii)<10 mbar; (iii)<1 mbar; (iv)<0.1 mbar; (v)<0.01 mbar; (vi)<0.001 mbar; (vii) 10-100 mbar; (viii) 1-10 mbar; (ix) 0.1-1 mbar; (x) 0.01-0.1 mbar; and (xi) 0.001-0.01 mbar.

The ion trap preferably further comprises a device arranged and adapted to maintain a substantially DC electric field in the first radial direction, wherein the DC electric field acts to retain at least some ions within the ion trap.

The linear ion trap preferably comprises one or more upper planar electrodes, one or more lower planar electrodes and a plurality of intermediate planar electrodes arranged between the one or more upper planar electrodes and the one or more lower planar electrodes.

According to the preferred embodiment:

(i) the one or more upper electrodes comprises a plurality of axially segmented upper electrode segments; and/or (ii) the one or more intermediate electrodes comprises a plurality of axially segmented intermediate electrode segments; and/or (iii) the one or more lower electrodes comprises a plurality of axially segmented lower electrode segments.

According to a less preferred embodiment the linear ion trap may comprise either: (i) a plurality of ring electrodes or other electrodes otherwise arranged so that ions pass, in use, through an aperture in or formed by the electrodes; or (ii) a multipole rod set comprising four, six, eight, ten or more than ten rods arranged in a longitudinal direction.

In a first mode of operation the ion trap may be operated as a differential ion mobility separator so that ions emerge from or are ejected from the differential ion mobility separator according to their differential ion mobility and wherein in a second mode of operation the ion trap may be operated either as: (i) an ion guide arranged so as to transmit ions without substantially separating ions according to either their differential ion mobility and/or their ion mobility; (ii) a collision, fragmentation or reaction device; or (iii) a device for separating ions according to their ion mobility.

The ion trap preferably further comprises a device arranged and adapted to increase, step, scan, or decrease an amplitude and/or time period of the asymmetric voltage waveform applied to the one more electrodes in order to increase, decrease or vary the radial separation or displacement of ions within the linear ion trap.

The ion trap preferably further comprises:

one or more entrance electrodes wherein, in use, a DC and/or RF potential is applied to one or more of the entrance electrodes in order to confine at least some ions axially within the linear ion trap in a mode of operation; and/or one or more exit electrodes wherein, in use, a DC and/or RF potential is applied to one or more of the exit electrodes in order to confine at least some ions axially within the linear ion trap in a mode of operation.

According to an aspect of the present invention there is provided a differential ion mobility separator comprising a linear ion trap as described above.

According to an aspect of the present invention there is provided a mass spectometer comprising a differential ion mobility separator as described above.

According to an aspect of the present invention there is provided a method of separating ions comprising:

providing a linear ion trap comprising a plurality of electrodes;

applying an asymmetric voltage waveform to one or more of the electrodes so that ions become radially separated according to their differential ion mobility; and forming an axial potential barrier at a position along the length of the linear ion trap so that ions having a first differential ion mobility and a first radial displacement are retained axially within the linear ion trap by the axial potential barrier whereas ions having a second different differential ion mobility and a second different radial displacement emerge axially or are ejected axially from the linear ion trap.

According to an aspect of the present invention there is provided a method of separating ions comprising:

providing a linear ion trap comprising a plurality of electrodes;

applying an asymmetric voltage waveform to one or more of the electrodes so that ions become radially separated in a first radial direction according to their differential ion mobility; and applying a symmetric RF voltage to one or more of the electrodes so that ions are confined within the ion trap in a second radial direction.

According to an aspect of the present invention there is provided a differential ion mobility separator comprising:

a plurality of electrodes;

a device arranged and adapted to apply an asymmetric voltage waveform to at least some of the plurality of electrodes in order to cause ions to become radially separated in a first radial direction according to their differential ion mobility;

a device arranged and adapted to apply a DC voltage to at least some of the plurality of electrodes in order create a DC electric field within the differential ion mobility separator in the first radial direction which acts to retain at least some ions within the differential ion mobility separator in the first radial direction;

a device arranged and adapted to apply a symmetric RF voltage to one or more of the electrodes so as to cause ions to be confined within the differential ion mobility separator in a second radial direction by a RF pseudo-potential field; and wherein the differential ion mobility separator is arranged and adapted to be maintained at a pressure <100 mbar.

According to an aspect of the present invention there is provided a method of separating ions according to their differential ion mobility comprising:

providing a plurality of electrodes; applying an asymmetric voltage waveform to at least some of the plurality of electrodes in order to cause ions to become radially separated in a first radial direction according to their differential ion mobility;

applying a DC voltage to at least some of the plurality of electrodes in order create a DC electric field within the differential ion mobility separator in the first radial direction which acts to retain at least some ions within the differential ion mobility separator in the first radial direction;

applying a symmetric RF voltage to one or more of the electrodes so that ions are confined within the differential ion mobility separator in a second radial direction by a RF pseudo-potential field; and maintaining the differential ion mobility separator at a pressure <100 mbar.

The preferred embodiment is particularly advantageous in that the linear ion trap or differential ion mobility separator is preferably operated at a pressure <100 mbar and ions are preferably confined in one radial direction by applying a symmetric RF voltage to some of the electrodes forming the ion trap or differential ion mobility separator. According to the preferred embodiment substantially no ions are lost as the differential ion mobility separator is scanned and the use of high voltage RF generators as is required for conventional differential ion mobility separators is avoided.

The preferred embodiment therefore represents a significant improvement compared with conventional differential ion mobility analysers.

According to the preferred embodiment the asymmetric voltage waveform and the symmetric RF voltage are simultaneously applied to the electrodes.

According to the preferred embodiment there is provided a high transmission RF ion guide wherein an applied electrical field or fields may be switched between two modes of operation. In a first mode of operation, the device preferably onwardly transmits a mass or mass to charge ratio range of ions. In a second mode of operation the device preferably acts as a linear ion trap in which ions are initially trapped and are then subsequently selectively displaced based upon their differential ion mobility characteristics in at least one radial direction. The ions may then be ejected sequentially in at least one axial or at least one radial direction.

The preferred device is preferably arranged and adapted to operate at sub-ambient pressures, preferably in the range $10^{-2}$ to 100 mbar, and more preferably in the range $10^{-1}$ to 10 mbar. Ions within the device are preferably confined by the use of inhomogeneous RF fields in one radial direction and a DC field in the other (orthogonal) radial direction.

Ions are preferably separated in a radial direction according to their differential ion mobility by applying an asymmetric voltage waveform in at least one radial direction.

According to an embodiment displaced ions may be ejected radially by allowing the ions to exit the device through one or more slots or grids provided in the upper or lower electrode structure.

According to another embodiment radially displaced ions may be ejected axially by means of one or more fixed radially dependant axial DC barriers. The position of the radially dependant axial DC barrier may vary with time.

In a preferred embodiment the RF ion guide preferably comprises a segmented flat plate ion guide, wherein the plates are arranged in a sandwich formation with the plane of the plates normal or parallel to the axis of the ion guide. A RF voltage is applied between neighbouring plates and is preferably of the same amplitude but is preferably 180° different in phase.

According to a less preferred embodiment the RF ion guide may comprise a ring stack comprising a plurality of ring electrodes wherein an RF voltage is applied between neighbouring ring electrodes. The RF voltage applied between neighbouring ring electrodes is preferably of the same amplitude but is preferably 180° different in phase. The individual ring electrodes may be formed from two or more segments allowing an asymmetric voltage waveform to be applied in one or more radial directions.

In another less preferred embodiment the ion guide may comprise an elongated RF multi-pole rod set such as a quadrupole or an octopole rod set.

The mass spectrometer preferably further comprises an ion source arranged upstream and/or downstream of the differential ion mobility separator, wherein the ion source is preferably selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("EI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; and (xx) a Glow Discharge ("GD") ion source.

The mass spectrometer may further comprise one or more continuous or pulsed ion sources. The mass spectrometer may further comprise one or more ion guides arranged upstream and/or downstream of the differential ion mobility separator. The mass spectrometer may further comprise one or more ion mobility separation devices and/or one or more Field Asymmetric Ion Mobility Spectrometer devices arranged upstream and/or downstream of the differential ion mobility separator.

The mass spectrometer may further comprise one or more ion traps or one or more ion trapping regions arranged upstream and/or downstream of the differential ion mobility separator. The mass spectrometer may further comprise one or more collision, fragmentation or reaction cells arranged upstream and/or downstream of the differential ion mobility separator, wherein the one or more collision, fragmentation or reaction cells are selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("ED") fragmentation device.

The mass spectrometer preferably further comprises a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser. The mass spectrometer may further comprise one or more energy analysers or electrostatic energy analysers arranged upstream and/or downstream of the differential ion mobility separator. The mass spectrometer preferably further comprises one or more ion detectors arranged upstream and/or downstream of the differential ion mobility separator.

The mass spectrometer may further comprise one or more mass filters arranged upstream and/or downstream of the differential ion mobility separator, wherein the one or more mass filters are selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter. The mass spectrometer may further comprise a device or ion gate for pulsing ions into the differential ion mobility separator. The mass spectrometer may further comprise a device for converting a substantially continuous ion beam into a pulsed ion beam.

The mass spectrometer may according to an embodiment further comprise: a C-trap; and an electrostatic mass analyser; wherein in a first mode of operation ions are transmitted to the C-trap and are then injected into the electrostatic mass analyser; and wherein in a second mode of operation ions are transmitted to the C-trap and then to a collision cell or Electron Transfer Dissociation and/or Proton Transfer Reaction device wherein at least some ions are fragmented into fragment ions, and wherein the fragment ions are then transmitted to the C-trap before being injected into the electrostatic mass analyser.

The mass spectrometer may further comprise a stacked ring ion guide comprising a plurality of electrodes having an aperture through which ions are transmitted in use and wherein the spacing of the electrodes increases along the length of the ion path. The apertures in the electrodes in an upstream section of the ion guide may have a first diameter and the apertures in the electrodes in a downstream section of the ion guide may have a second diameter which is smaller than the first diameter. Opposite phases of an AC or RF voltage are preferably applied to successive electrodes.

BRIEF DESCRIPTION OF THE DRAWINGS

Various embodiments of the present invention will now be described, by way of example only, together with other arrangements given for illustrative purposes only, and with reference to the accompanying drawings in which.

DETAILED DESCRIPTION OF THE PREFERRED EMBODIMENTS

Figure 1:
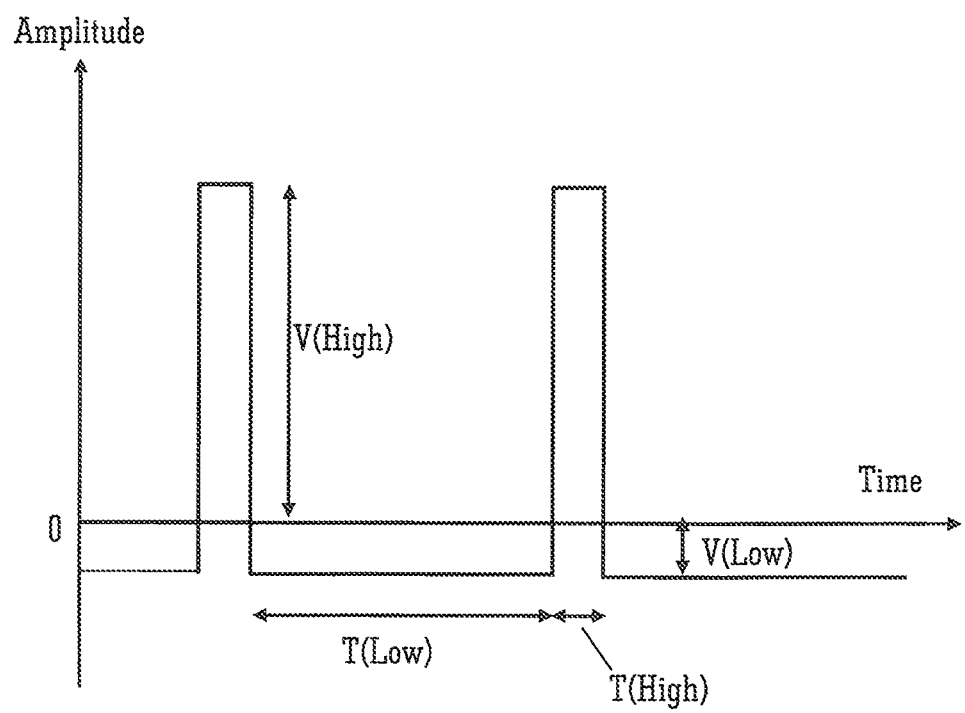
FIG. 1 illustrates the form of a conventional asymmetric voltage waveform used to provide differential mobility separation wherein V(High)° T(High)equals V(Low)*T(Low)
Figure 2A:
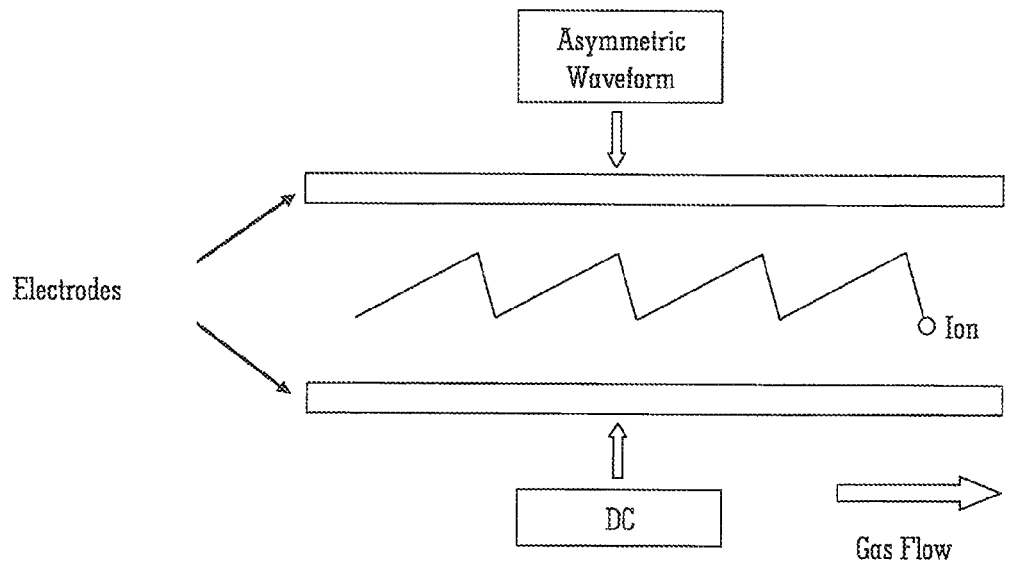
FIG. 2A illustrates the trajectory of an ion through a pair of electrodes forming a conventional FAIMS device wherein an asymmetric voltage waveform is applied to the electrodes and wherein the high and low field mobilities of the ion are the same so that the net ion motion is in a direction parallel to the plates and FIG. 2B illustrates the trajectory of an ion through a pair of electrodes of a conventional FAIMS device wherein an asymmetric voltage waveform is applied and wherein the high and low field mobilities of the ion are different so that the net ion motion is in a direction towards one of the plates.
Figure 2B:
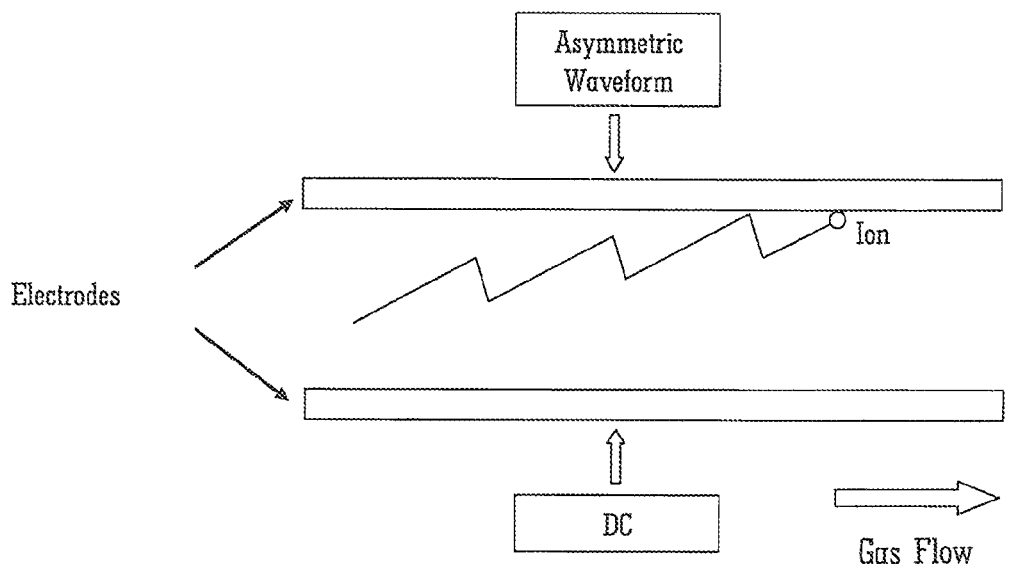

FIG. 1 shows a known asymmetric potential difference which may be applied between the plates of a known ion mobility separator in order to separate ions according to their differential ion mobility. The product of voltage*time is arranged to be the same for the low and high field sections of the wave. Consequently, if the low and high field mobility of an ion species are the same then the average trajectory of an ion will be parallel to the plates and the ion will be transmitted through the device as shown in FIG. 2A. However, if the low and high field mobilities differ, then the ion will drift towards one or other of the plates and be lost to the system as shown in FIG. 2B. Through application of a DC voltage to one plate it is possible to compensate for any mobility-induced drift and to allow transmission of ions having a desired differential ion mobility.

A preferred embodiment of the present invention will now be described with reference to FIG. 3. A stacked plate ion guide is preferably provided wherein a sinusoidal confining RF potential 4 is preferably applied to intermediate RF plate electrodes 3 in order to confine ions in a first (x) radial direction by a pseudo-potential field. A DC voltage is preferably applied between the upper and lower electrodes 2 in order to confine ions in the second (y) radial direction by virtue of a real potential field.

Advantageously, the restoring or confining force in the vertical (y) direction is not mass or mass to charge ratio dependent.

Figure 3:
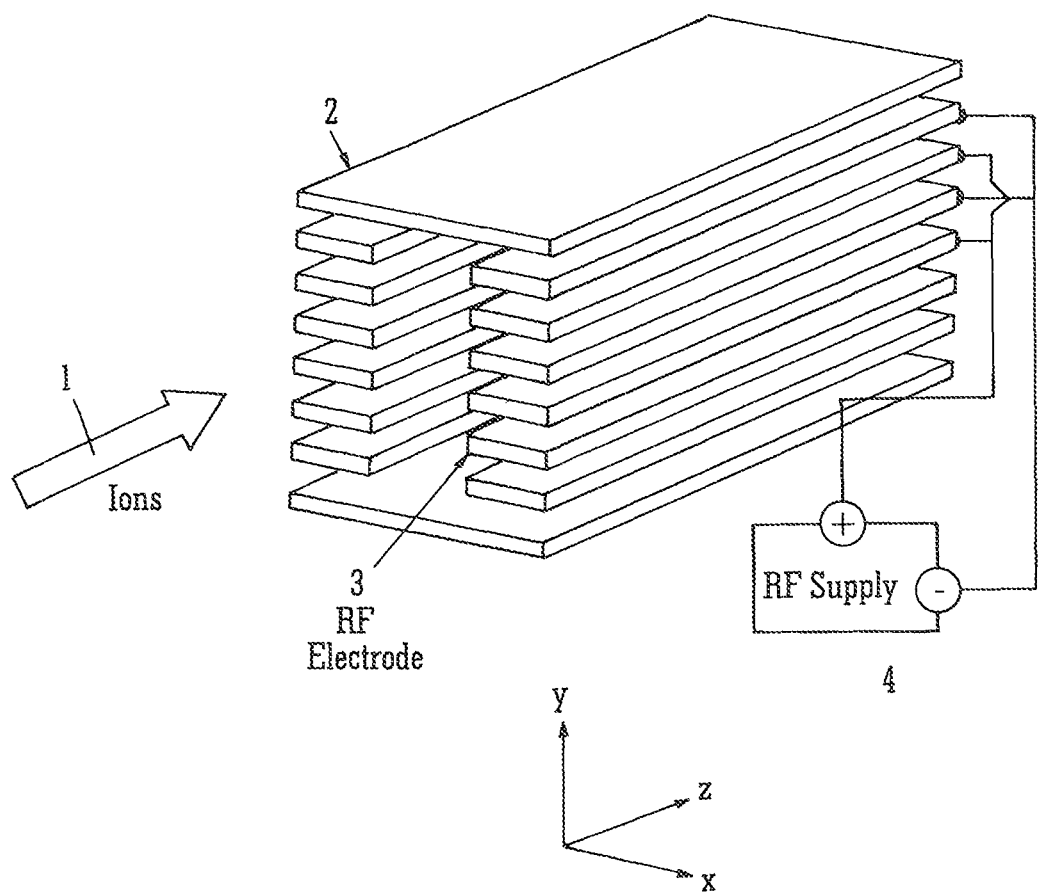
FIG. 3 shows the basic arrangement of a stacked plate ion trap according to an embodiment of the present invention.
Figure 4:
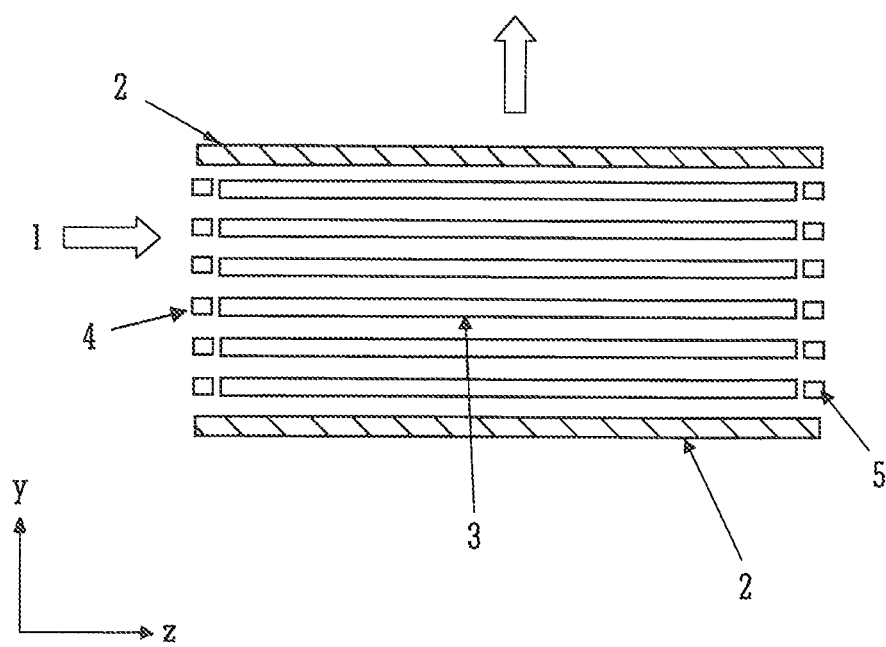
FIG. 4 shows a stacked plate ion trap in the y,z plane according to an embodiment wherein ions are ejected radially from the ion trap via an aperture in the upper plate electrode.

FIG. 4 shows a modification of the general device shown in FIG. 3 in the y,z plane. According to this embodiment ions are ejected radially in the vertical (y) direction from the device via a longitudinal slit in the upper electrode 2 (not shown in FIG. 3). The intermediate RF electrodes 3 are also preferably axially segmented at the front and rear of the device to form entrance electrodes 4 at the entrance to the device and exit electrodes 5 at the exit of the device. All or some of the entrance electrodes 4 and/or all or some of the exit electrodes 5 are preferably supplied with the same confining RF voltage as is applied to the other intermediate RF plate electrodes 3. An additional DC voltage may be applied to all or some of the entrance electrodes 4 and/or to all or some of the exit electrodes 5 in order to cause ions to be confined in the axial (z) direction within the device so that the device may be operated as an ion trap in a mode of operation.

During a period of time during which ions 1 enter the device, the entrance electrodes 4 are preferably supplied with a DC potential which is preferably low enough so as to allow ions to enter the device. The exit electrodes 5 are preferably held at a potential which is preferably high enough to prevent ions from exiting the device. When sufficient ions have been stored within the device, the entrance electrodes 4 are then preferably supplied with a DC potential which is preferably high enough to prevent ions from exiting the device. Simultaneously, further ions are preferably prevented from entering the device. Ions prevented from entering the device during an analytical scan of the device may be accumulated in an additional ion trapping device (not shown) which may be arranged upstream of the differential ion mobility ion trap. This ensures efficient utility of the ions generated by the ion source.

Ions within the device are effectively confined in a first radial (x) direction by a pseudo-potential field provided by the intermediate RF plate electrodes 3 and in a second (y) radial direction by a DC potential well provided by a DC potential applied to the upper and lower electrodes 2.

Once ions have been trapped within the device, an asymmetric voltage waveform is then preferably applied to the upper and/or lower electrodes 2. The asymmetric voltage waveform may have a dipolar form and according to an embodiment is applied to either the upper electrode or the lower electrode but not to both electrodes. The asymmetric voltage waveform preferably does not have the effect of confining ions radially within the device. The amplitude of the asymmetric voltage waveform may then be continuously increased, stepped or scanned in order to effect sequential separation and displacement of the ions in the vertical (y) radial direction with respect to their differential ion mobility. Ions may then exit the trapping volume radially by passing through one or more slots or apertures in the upper and/or lower electrodes 2 (the slot or aperture is not shown in FIG. 3). Alternatively, the upper and/or lower electrodes 2 may be constructed from one or more grid or mesh electrodes which preferably allow ions to pass therethrough once the ions have been displaced radially to a sufficient degree. The relative time at which ions exit the device is related to their differential ion mobility characteristic. Ions exiting the device are preferably onwardly transmitted for further analysis and or detection.

Figure 5:
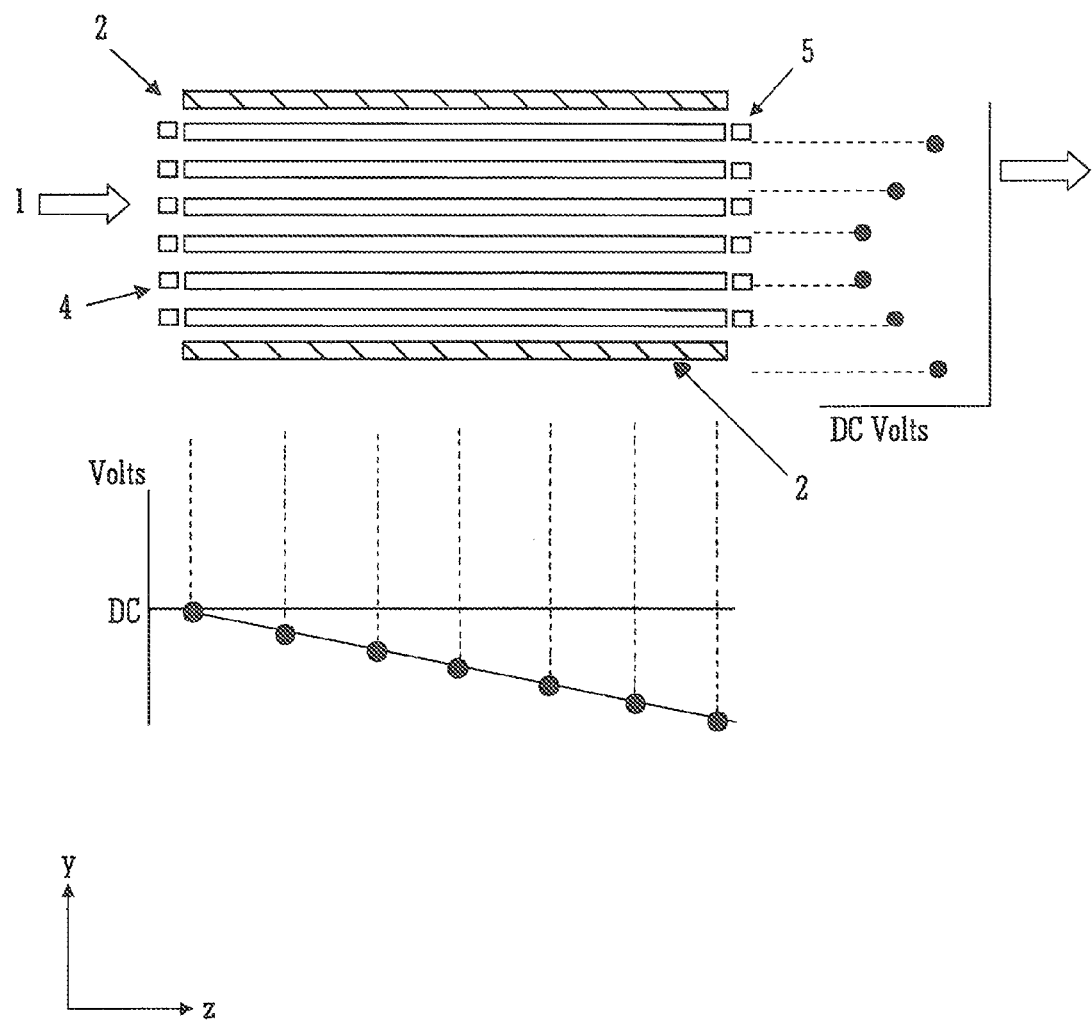
FIG. 5 shows a stacked plate ion trap in the y,z plane according to another embodiment illustrating potentials applied to the upper and lower electrodes and exit electrodes in order to effect axial ejection of radially displaced ions.

FIG. 5 shows a preferred embodiment of the device wherein radially displaced ions are subsequently ejected axially from the device. The device is shown in the y,z plane. Ions are first trapped within the device in a similar manner as described above in relation to the embodiment shown and described with reference to FIG. 4.

FIG. 5 shows the potentials applied to the device prior to an analytical scan according to an embodiment of the present invention. An axial DC potential gradient is preferably maintained along the length of the upper and lower DC plate electrodes 2 in order to urge ions axially towards the exit of the device. The axial DC voltage gradient may be achieved by axially segmenting the upper and lower plate electrodes 2 (axial segments not shown in FIG. 5) or, more preferably, by applying a resistive coating to the inner surface of the upper and lower electrodes 2.

The DC potentials applied to the individual elements of the exit electrodes 5 are preferably arranged such that the exit electrodes 5 closest the central axis of the device provide a higher axial trapping potential than those exit electrodes 5 which are further away from (or radially displaced from) the central axis in the vertical (y) direction. In one embodiment the exit electrodes 5 may take the form of a parallel wire grid which extends across the device in the horizontal (x) direction in the y,x plane.

As a result, a (horizontal) DC potential barrier is preferably provided at the exit region of the device which preferably prevents ions arranged along the central axis from exiting the device. The profile of the DC potential barrier at the exit of the device is preferably such that the DC potential barrier is higher near the central axis of the device and is lower or becomes effectively zero (or becomes an extractive field) further away from the central axis of the device in the vertical (y) radial direction.

The amplitude of an asymmetric voltage waveform applied between the upper and lower electrodes 2 is preferably continuously increased, stepped or scanned in order to effect sequential separation and displacement of ions in the vertical (y) direction with respect to their differential ion mobility.

As ions become displaced from the central axis in the vertical (y) direction, ions are also preferably urged towards the exit region wherein the ions will preferably experience a reduced exit DC potential barrier provided by the exit electrodes 5. As a result, when the force acting on the ions in the axial (z) direction is sufficient to overcome the confining DC potential barrier applied to the exit electrodes 5, then the ions will exit the device in an axial direction. The relative time at which ions exit the device is preferably related to their differential ion mobility characteristic.

Other methods of axial ejection are also contemplated.

Figure 6:
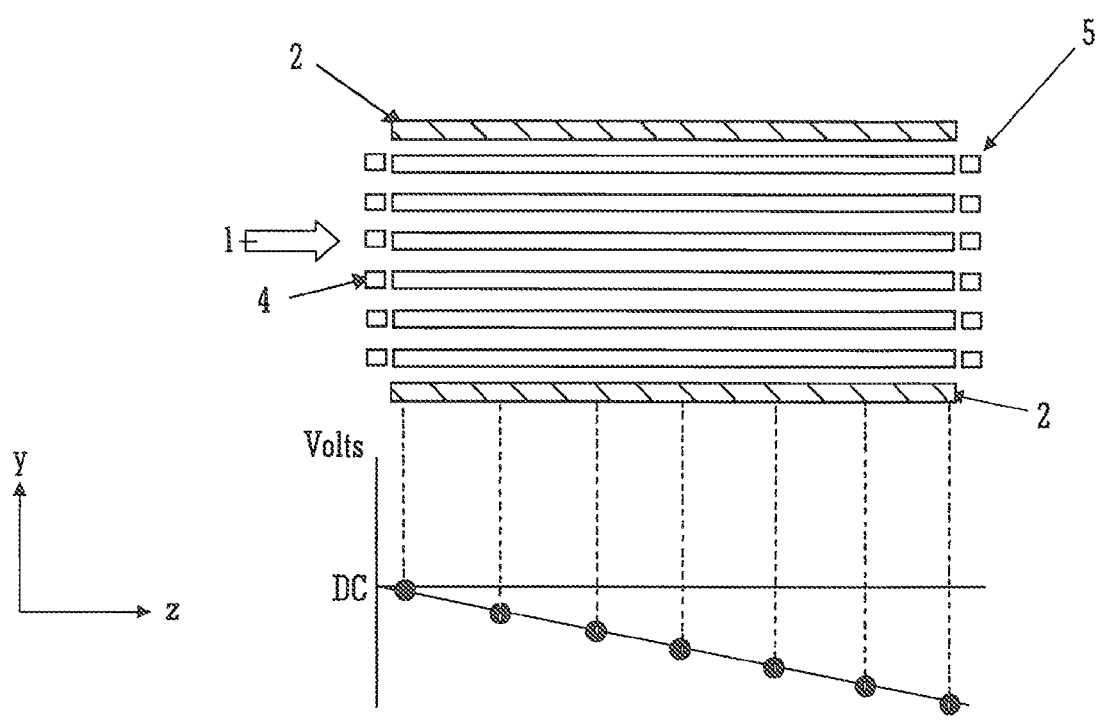
FIG. 6 shows a stacked plate ion trap in the y,z plane illustrating an axial DC voltage gradient maintained along the upper and lower electrodes.

In a less preferred embodiment axial ejection of ions which have been radially separated according to their differential ion mobility may be effected by modifying the DC potential applied to both the upper and lower DC plate electrodes 2 and the intermediate RF confining plate electrodes 3 such that an axial field is produced which is substantially zero on the central axis of the device and which preferably increases with deviation or displacement from the central axis of the device in both the horizontal (x) and vertical (y) directions. The form of the DC potential applied to the upper and lower DC plate electrodes 2 is shown in FIG. 6. The axial DC potential applied to both the upper and lower plates 2 in FIG. 6 decreases from the entrance to the exit of the device. Over the entire length of the device the DC voltage applied to the upper and lower plate electrodes 2 is preferably sufficient so as to confine ions within the device and drive ions towards the exit of the device.

Figure 7:
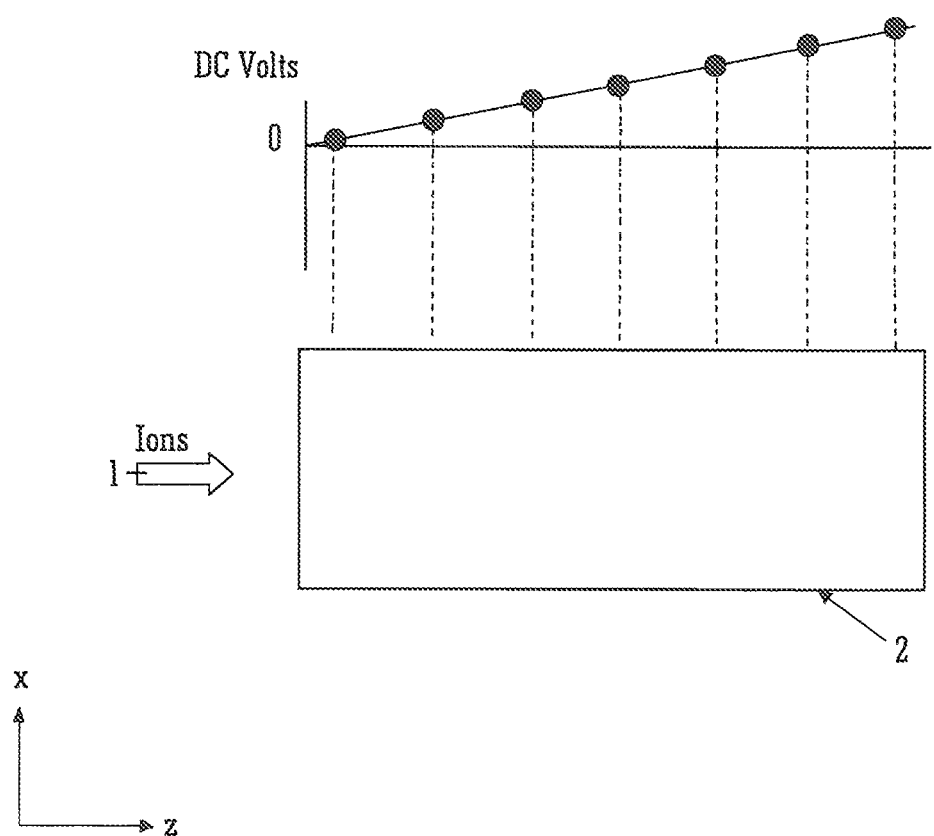
FIG. 7 illustrates a DC voltage gradient maintained along the intermediate RF electrodes.

FIG. 7 shows the same device as described above with reference to FIG. 6 but in the x,z plane. The form of a DC potential applied to the intermediate RF plate electrodes 3 in addition to the RF potential is shown in FIG. 7. The DC potential applied to the intermediate electrodes 3 increases from the entrance to the exit of the device. This potential results in a DC field which acts to drive ions which become displaced radially in the x-direction (horizontal) back towards the entrance of the device. The DC potentials may be maintained by segmenting both the intermediate RF electrodes 3 and also the upper and/or lower DC electrodes 2 or, more preferably, by applying a resistive coating to the inner surface of the intermediate RF electrodes 3 and the upper and lower DC electrodes 2.

The combination of these two fields is preferably sufficient to produce a resultant field within the device which preferably acts to drive ions towards the exit of the device when ions become displaced vertically from the central axis in the vertical (y) direction by virtue of their differential ion mobility and which acts to drive ions back towards the entrance of the device when ions are displaced sideways in the horizontal (x) direction.

Ions displaced vertically from the central axis in the vertical (y) direction, as the amplitude of the asymmetric voltage waveform applied to the upper and lower plate electrodes 2 is increased during an analytical scan, will experience an axial field acting towards the exit of the device. When the force acting on the ions in the axial (z) direction is sufficient to overcome the confining DC barrier applied to the exit electrodes 5, then the ions will exit the device. The time at which ions exit the device will be related to their differential ion mobility characteristic. It should be noted that although the radial displacement of the ions is predominantly related to characteristic differential ion mobility, the transit time of ions in the axial (z) direction as they exit the device will be related to their ion mobility.

Figure 8:
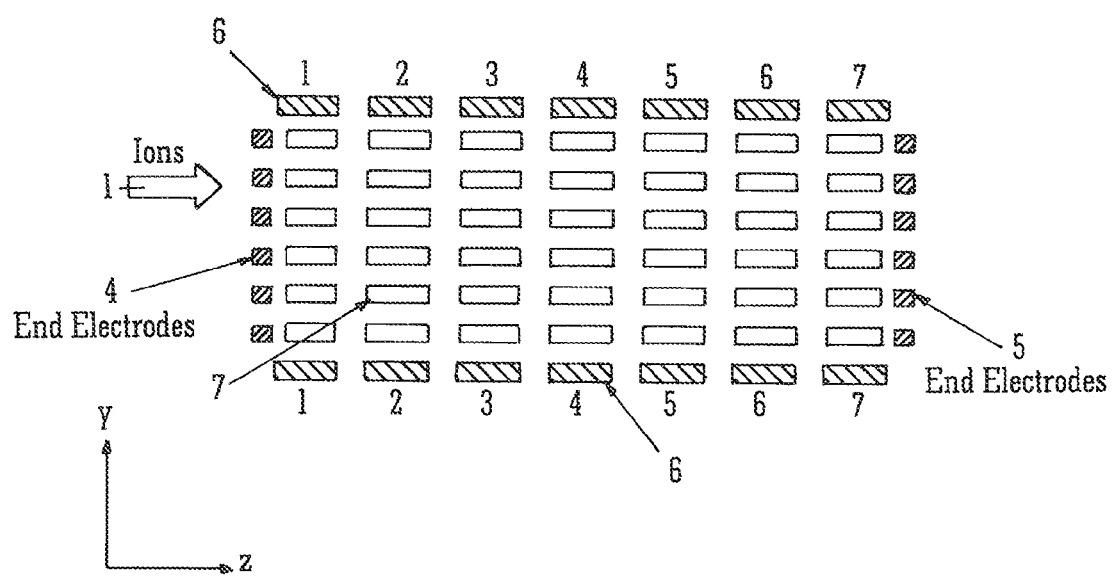
FIG. 8 shows an embodiment wherein the upper and lower electrodes and the intermediate RF electrodes are axially segmented.

In a less preferred embodiment described with reference to FIG. 8, axial ejection of ions which have been separated according to their differential ion mobility may be effected by applying a first travelling or transient DC voltage waveform to the upper and lower DC plate electrodes 6 and a second travelling or transient DC voltage waveform to the intermediate RF confining plate electrodes 7. The first and second transient DC voltage waveforms preferably act in opposing axial (z) directions. FIG. 8 shows an embodiment, in the y,z plane, wherein the upper and lower DC confining plate electrodes 6 and the RF confining plate electrodes 7 are segmented allowing application of separate travelling DC voltage waves to the different electrodes.

Figure 9:
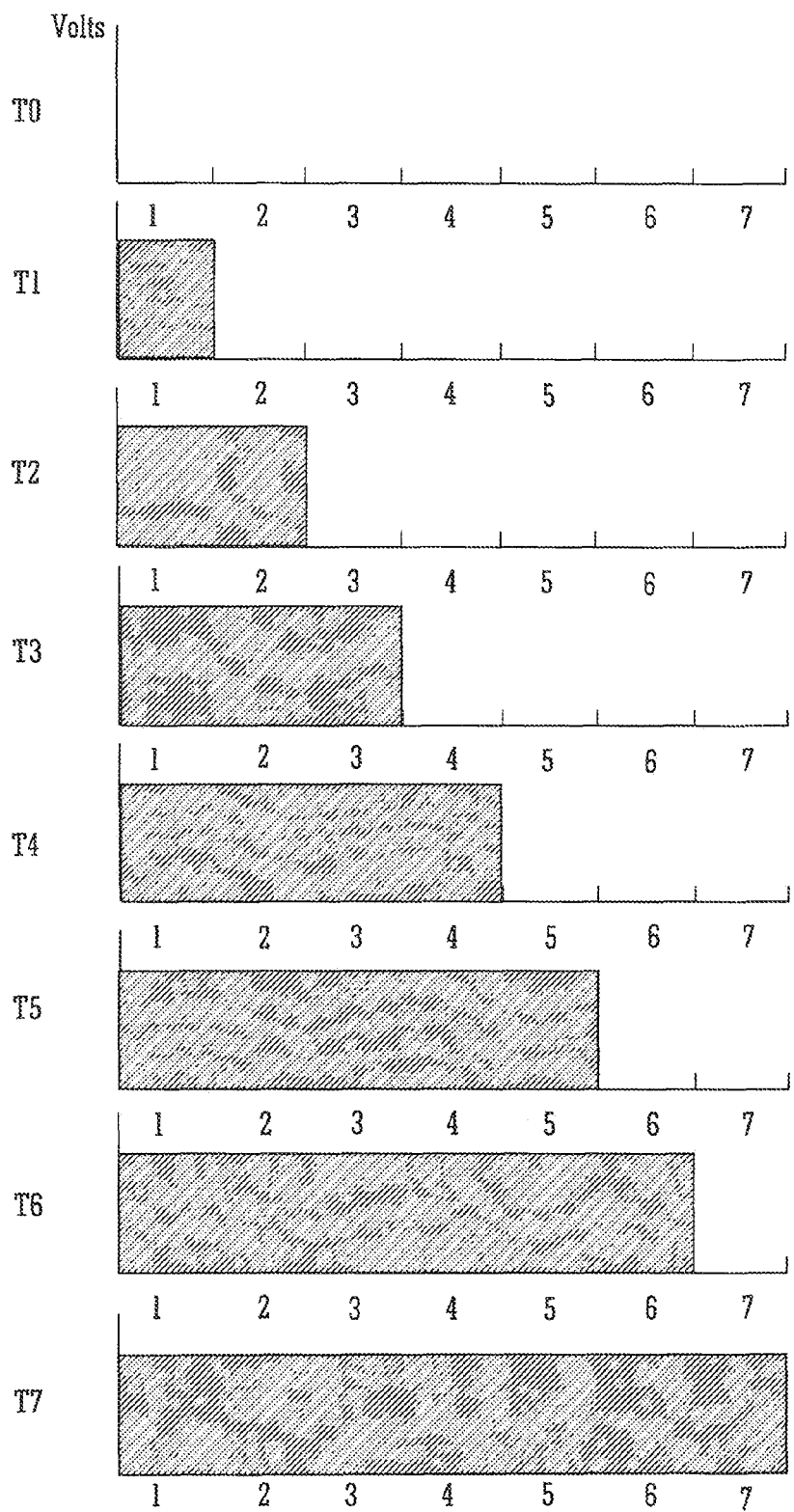
FIG. 9 shows a first time varying potential applied to the upper and lower electrodes according to an embodiment.
Figure 10:
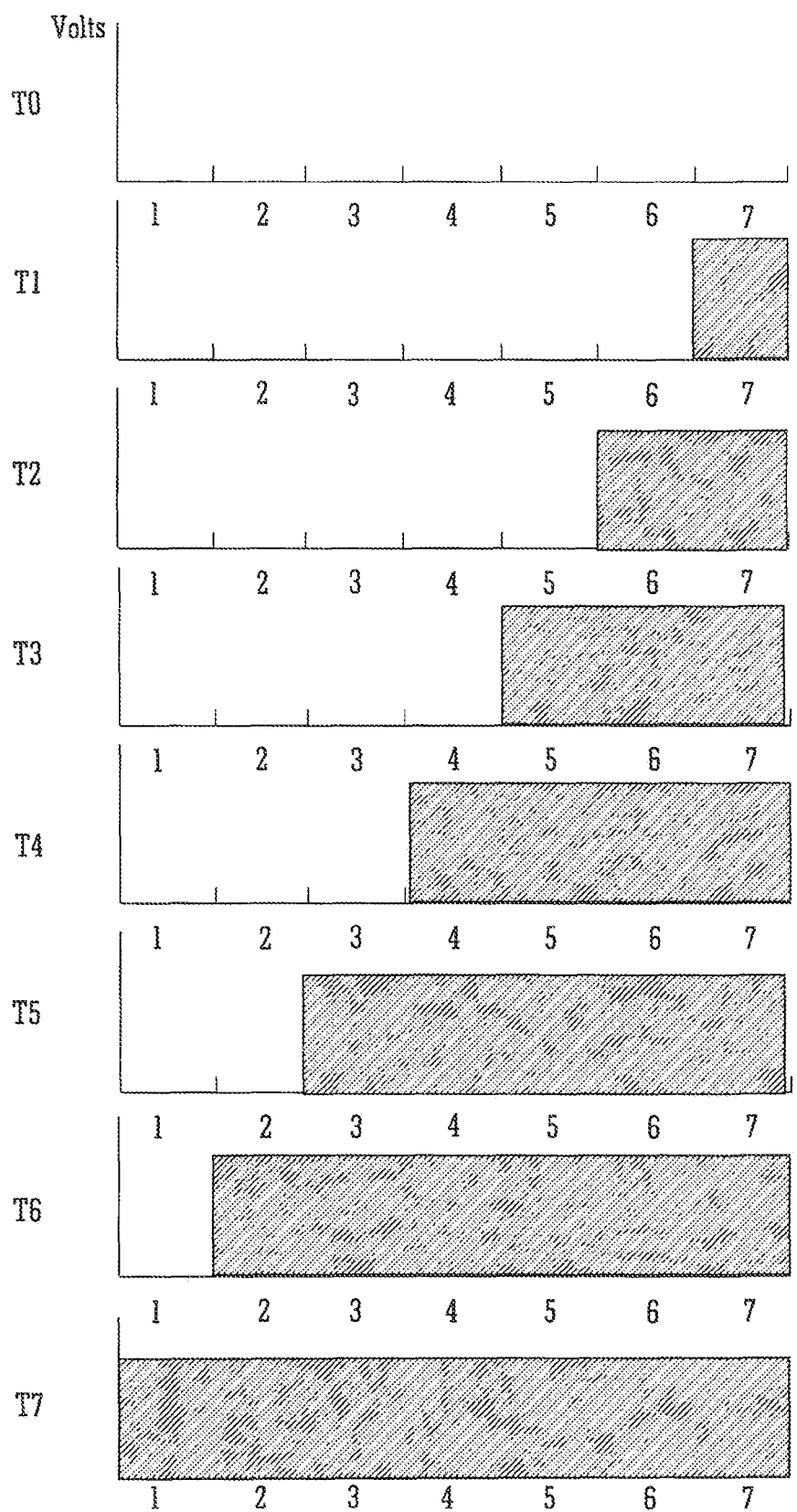
FIG. 10 shows a second time varying potential applied to the intermediate RF electrodes according to an embodiment.

FIG. 9 shows the form of a first travelling or transient DC voltage waveform which may be applied to the upper and lower electrodes 6 during a time period from T0 to T7 (wherein T0<T7) and FIG. 10 shows the form of a corresponding second travelling or transient DC voltage waveform which may be applied to the intermediate RF electrodes 7 during the same time period from T0 to T7. Ions near the central axis of device will experience no net force in the axial (z) direction. However, ions displaced vertically from the central axis in the vertical (y) direction, as the amplitude of the asymmetric voltage waveform applied to all of the segmented plate electrodes 6 is increased during an analytical scan, will be driven towards the exit of the device. When the force acting on the ions in the axial (z) direction is sufficient to overcome the confining DC barrier applied to the exit electrodes 5 then the ions will exit the device. The time at which ions exit the device will be related to their differential ion mobility characteristic.

Whilst the ion transport volume of the stacked plate ion guide preferably has a rectangular cross-section, other cross-sectional forms may be used and/or the cross-sectional form may vary along the length of the device.

Through use of combined RF and DC confining fields, the device can be operated as an ion guide or ion trap at sub-ambient pressures whilst minimising diffusive loss. A benefit of operating the device at relatively low gas pressure is that the voltage difference required between the upper and lower plate electrodes in order to achieve high E/N values reduces in proportion to the pressure. In general, conventional differential ion mobility analysers operate with electric fields of tens of kilovolts per cm. Therefore, by scaling, tens of volts per cm at the millibar pressure level is, advantageously, adequate to produce non-linear mobility effects according to embodiments of the present invention.

Another advantage of the preferred device is that the asymmetric voltage waveform applied to the upper and lower plate electrodes 2 can be changed to a symmetric waveform, or to a DC voltage, such that the device can be operated solely as an ion guide or an ion mobility separator in an alternative mode of operation.

Figure 11:
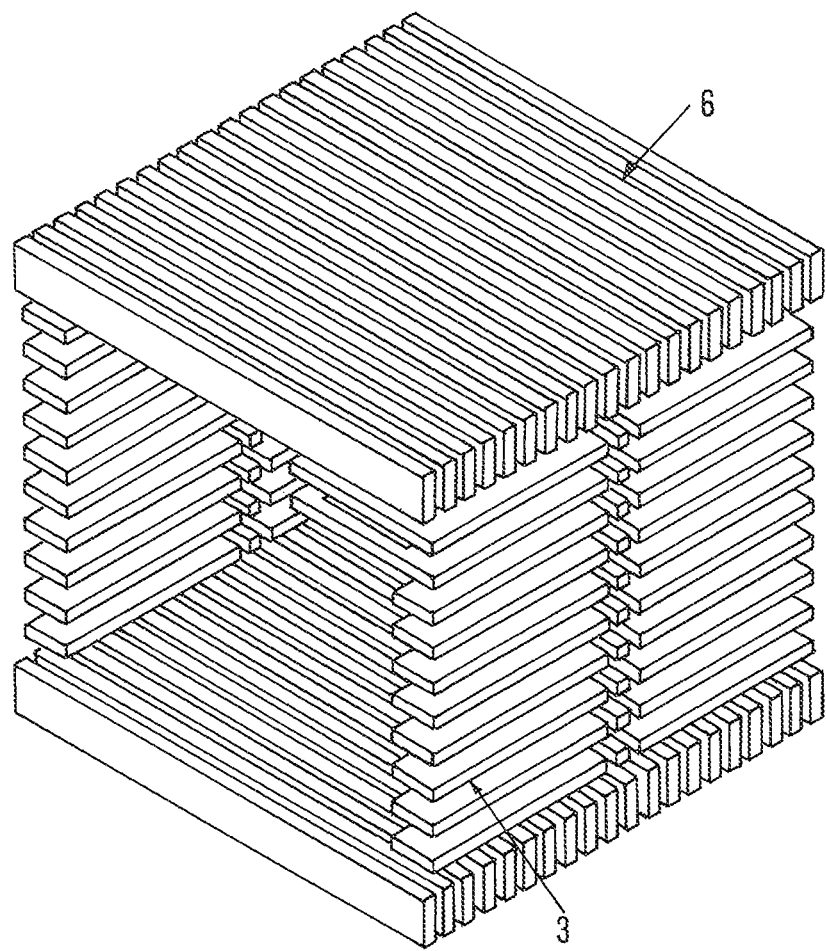
FIG. 11 shows a stacked plate ion trap which was used in a SIMION® ion trajectory model.
Figure 11:
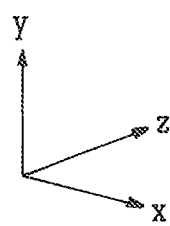

A SIMION® model was used to evaluate the capabilities of an asymmetric field for axial ion ejection based on differential ion mobility separation in a stacked plate ion trap. The geometry which was used is shown in FIG. 11. The stacked plate ion trap had an internal dimension of 16 mm in the x direction, 18 mm in the y direction and 19 mm in the z direction. The intermediate RF confining plate electrodes 3 were arranged to be 0.5 mm thick and were arranged with a centre-to-centre spacing of 1.5 mm. The upper and lower plate electrodes 6 were segmented axially with each segment having a width of 0.6 mm and a centre to centre spacing of 0.8 mm.

Figure 12:
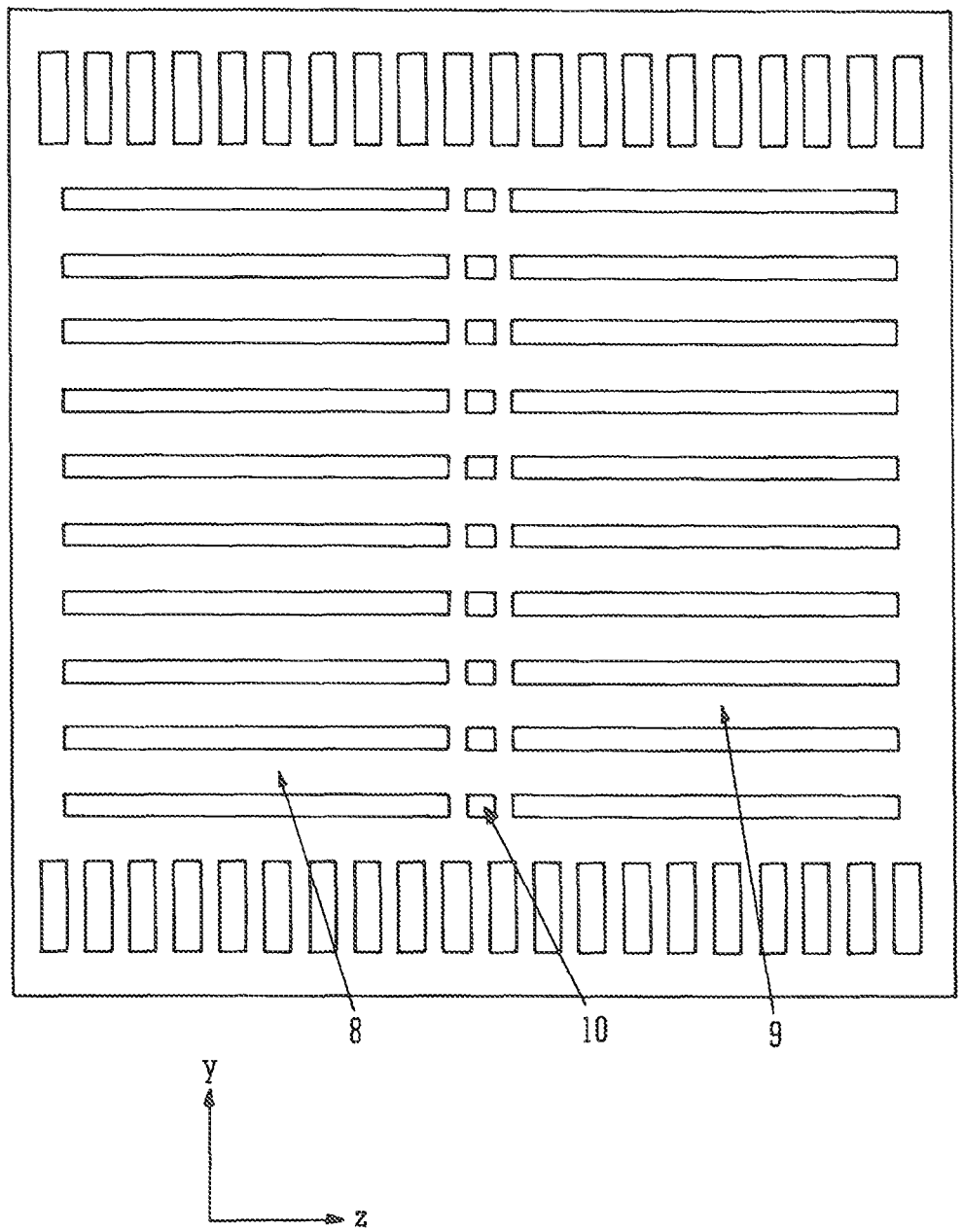
FIG. 12 shows the stacked plate ion trap model in the y,z plane.

FIG. 12 shows the model in the y,z plane. The intermediate RF electrodes were arranged to form two sections 8,9. The two sections 8,9 were separated from each other by barrier electrodes 10. The first section 8 comprised an analytical ion trapping section and the second section 9 was arranged to act as an ion guide section.

Figure 13:
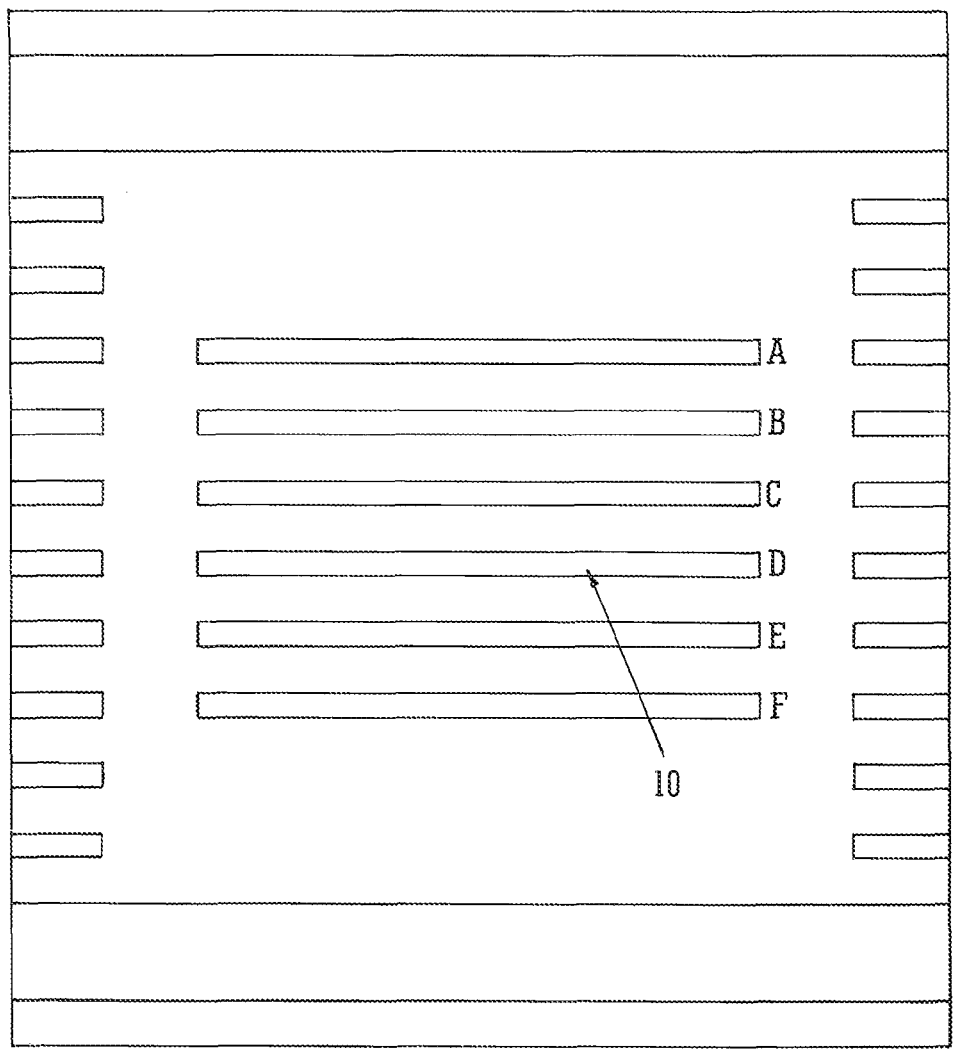
FIG. 13 shows the stacked plate ion trap model in the y,x plane.

FIG. 13 shows the SIMION® model in the y,x plane. Barrier electrodes A-F are shown extending into the device in the x,y plane. The barrier electrodes A-F represent elements of a substantially transparent parallel wire grid which separates first section 8 from second section 9.

Figure 14:
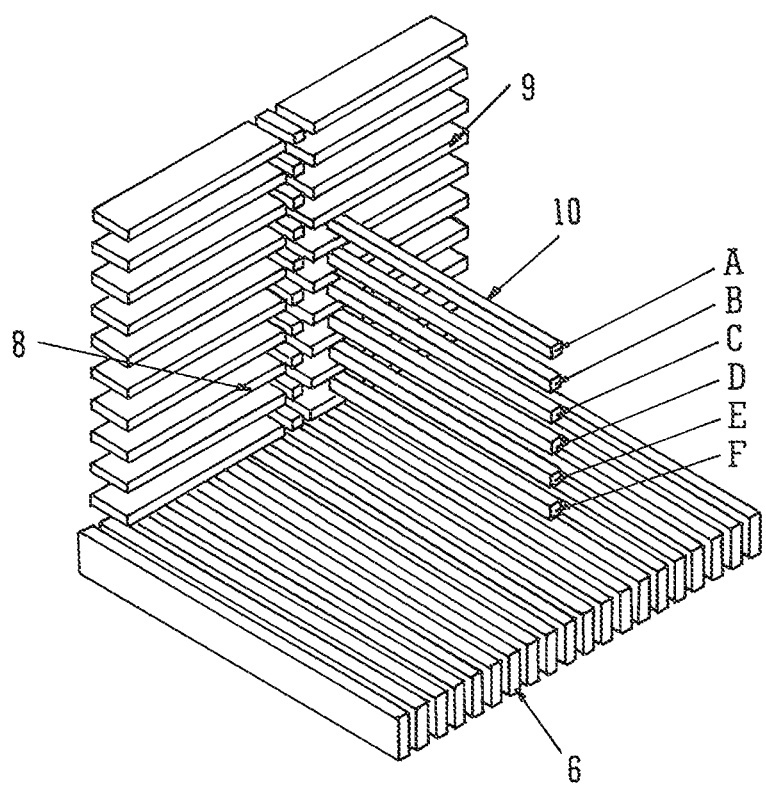
FIG. 14 shows the model with electrode structures cut away to reveal the inner electrode structure.
Figure 14:
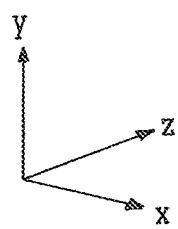

FIG. 14 shows the model with a portion of the electrode structure cut away to reveal the inner structure including the relative position of the barrier electrodes 10. The barrier electrodes 10 A-F were maintained at DC potentials A=0 V, B=4 V, C=2 V, D=2 V, E=4 V and F=0 V. The intermediate RF confining electrodes bounding the first section 8 were supplied with a 400 V pk pk RF waveform at a frequency of 1 MHz RF. The intermediate RF confining electrodes bounding the second section 9 were also supplied with a 400 V pk pk RF waveform at a frequency of 1 MHz RF and were also maintained at a DC offset voltage of −2 V. The combination of the DC voltages applied to the barrier electrodes 10 and the RF confining electrodes bounding the second region 9 resulted in a potential barrier in the centre of the device which reduced to zero with displacement in the vertical (y) direction away from the central axis. Upper and lower segmented plate electrodes 6 were maintained at a linear potential gradient extending from the entrance to exit of the device. The potential gradient resulted in an axial field gradient which acted to urge ions towards the potential barrier produced by the barrier electrodes 10. A pressure of nitrogen gas of 1 Torr was simulated within the device using a simple viscous damping model.

Figure 15:
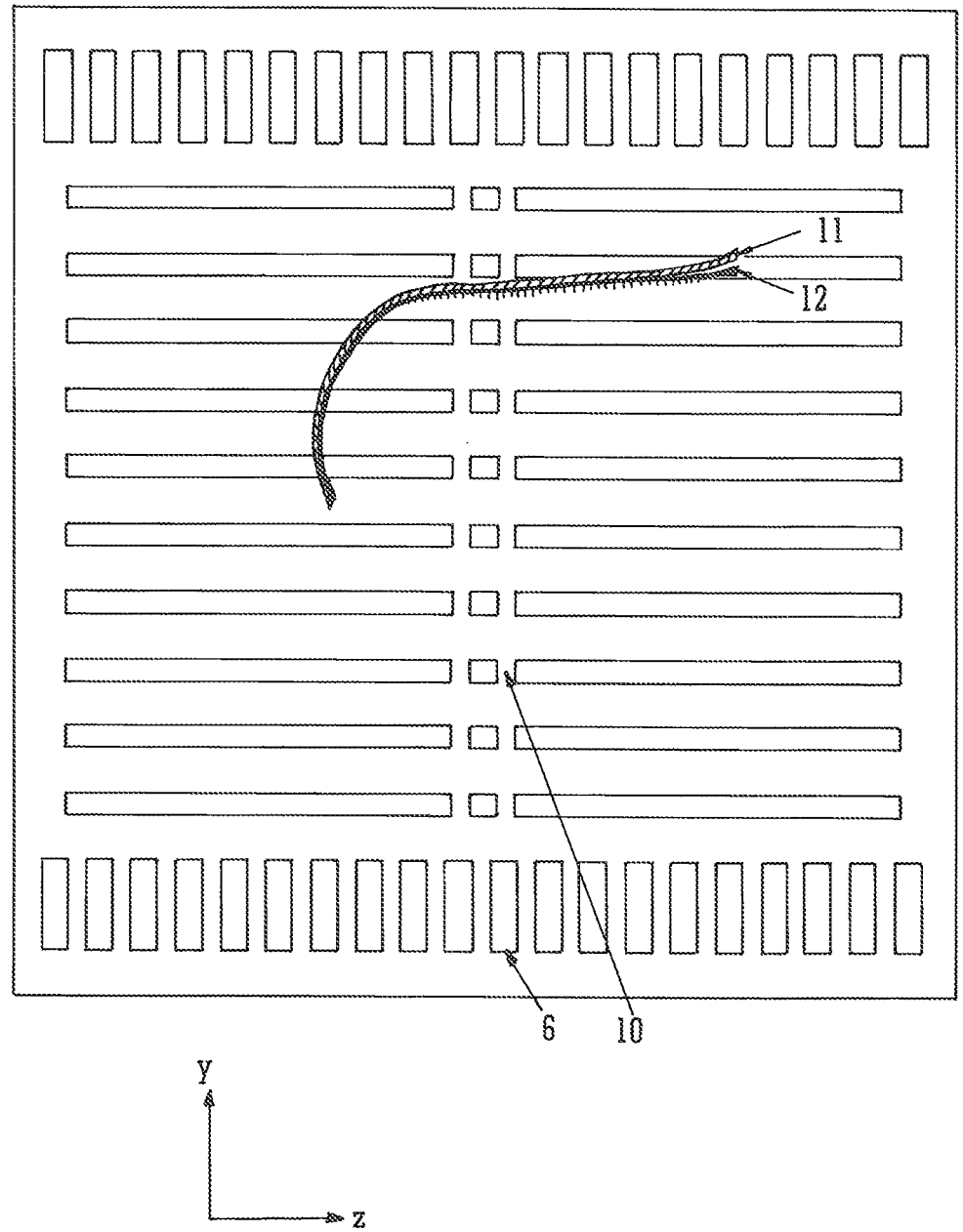
FIG. 15 shows ion trajectories within the model during an analytical scan.

FIG. 15 shows the trajectory of two ions trapped within the device when an asymmetric voltage waveform was applied between the upper and lower segmented electrodes 6. The asymmetric voltage waveform was applied with a frequency f of 750 MHz. From FIG. 1, V(high) was applied for time T(High) wherein:

$$T(\text{High}) = 0.3 \times \frac{1}{f} \quad (2)$$

V(low) is given by:

$$V(\text{Low}) = V(\text{High}) \times \frac{0.3}{0.7} \quad (3)$$

and was applied for time T(Low) where:

$$T(\text{Low}) = 0.7 \times \frac{1}{f} \quad (4)$$

At time T=0 ions were introduced into the ion trap and were allowed to equilibrate to positions near the central potential barrier. At subsequent time T=1, wherein T1>T0, the amplitude of an asymmetric voltage waveform applied to the upper and lower electrodes 6 was increased to 98 V and was then ramped at a rate of 4.9 V/ms for 10 ms.

To approximate the motion of two ions with differing mobility characteristics, ion mobility was modelled according to the equation:

$$K\left(\frac{E}{N}\right) = K_0\left[1 + \alpha\left(\frac{E}{N}\right)^2 + \beta\left(\frac{E}{N}\right)^4\right] \quad (5)$$

wherein $K_0$ is the low E/N mobility.

Referring to FIG. 15, the first ion 11 was assigned a mass to charge ratio of 173 with $K_0$=1.81, $\alpha$=7.984×10$^{-6}$ Td$^{-2}$ and $\beta$=−3.049×10$^{-10}$ Td$^{-4}$. The values of $\alpha$ and $\beta$ were taken from a reference paper (Guevremont et al., J Am Soc Mass Spectrom., 2005, 16, 349-362). The value of $K_0$ was set arbitrarily. The second ion 12 was assigned a mass to charge ratio of 386.62 with $K_0$=1.24, $\alpha$=−2.16×10$^{-6}$ Td$^{-2}$ and $\beta$=−0.84× 10$^{-10}$ Td$^{-4}$. The values of $\alpha$ and $\beta$ were taken from a reference paper (Prasad et al., Anal Chem. 2009, 81, 8749-8757). The value of $K_0$ was set arbitrarily.

The values of the constants assigned to the ions were not intended to relate to any measured physical characteristics of particular species. The values were chosen to be realistic values allowing the principle of operation to be demonstrated.

The first ion 11 was observed to pass the central trapping barrier of the device 10 after 4 ms. The second ion 12 was observed to pass the central trapping barrier of the device 10 after 8 ms. Once the ions had crossed the central barrier they may then be onwardly transmitted for further analysis or detection.

Other less preferred embodiments are contemplated wherein RF potentials may be applied to the confining plate electrodes in the y direction in order to produce a pseudo-potential confining field in the y direction. In this case radial separation of ions will be related to both their differential ion mobility and also their mass or mass to charge ratio.

Another embodiment is contemplated wherein a RF potential may be applied to the barrier electrodes 10 so as to produce a mass to charge ratio dependent pseudo-potential barrier between the two regions 8,9.

The ions entering the device may come from a variety of different ionisation sources and may be entrained in a gas flow or entering from vacuum. The ion sources may, for example, comprise an Electrospray, an Atmospheric Pressure Chemical Ionisation, an Atmospheric Pressure Photoionisation, a MALDI, an Inductively Coupled Plasma, an Electron Impact or a Chemical Ionisation ion source.

The ions exiting the device may be detected directly or may be subject to further analysis prior to detection. Possible further analysis includes but is not limited to mass spectrometry, tandem mass spectrometry, Ion Mobility Spectrometry or combinations thereof.

Whilst the asymmetric voltage waveform has been shown as being rectangular, other forms of asymmetric field may be used to effect separation according to other embodiments of the present invention.

Whilst the ion transport volume shown in the stacked plate ion guide as described has a rectangular cross-section, other cross-sectional forms may be used. Embodiments are also contemplated wherein the cross-sectional form may vary throughout the length of the device.

The device may also be used as a standard ion mobility drift cell in a mode of operation.

Improvements in performance of the differential ion mobility device may be achieved by modifying the buffer gas by addition of dopant gasses or vapours.

Although the present invention has been described with reference to the preferred embodiment, it will be understood by those skilled in the art that various changes in form and detail may be made without departing from the scope of the invention as set forth in the accompanying claims.

The invention claimed is:
1. A linear ion trap comprising:
a plurality of longitudinally extending, stacked electrodes;
a device arranged and adapted to apply an asymmetric voltage waveform to one or more of said electrodes so that, in use, ions become radially separated in a first radial direction according to their differential ion mobility; and
a device arranged and adapted to form, in use, a DC axial potential barrier at a position along the axial length of said linear ion trap so that ions having a first differential ion mobility and a first radial displacement are retained axially within said linear ion trap by said axial potential barrier whereas ions having a second different differential ion mobility and a second different radial displacement emerge axially or are ejected axially from said linear ion trap when a force acting on the ions having the second different differential ion mobility in the axial direction is sufficient to overcome the DC axial potential barrier applied to exit electrodes;
wherein said linear ion trap is operated or maintained, in use, at a pressure <100 mbar.
2. A linear ion trap as claimed in claim 1, further comprising a device arranged and adapted to apply a symmetric RF voltage to one or more of said electrodes so that, in use, ions are confined within said ion trap in a second radial direction by a RF pseudo-potential field.
3. A linear ion trap as claimed in claim 2, wherein said second radial direction is orthogonal to said first radial direction.
4. A linear ion trap as claimed in claim 1, further comprising a device arranged and adapted to maintain an axial DC potential gradient along at least a portion of the axial length of said linear ion trap in a mode of operation in order to urge at least some ions in a first axial direction along said linear ion trap.

5. A linear ion trap as claimed in claim 1, further comprising a device arranged and adapted:
   (i) to apply one or more transient DC voltages or one or more transient DC voltage waveforms to at least some first electrodes in order to urge at least some ions having a first radial displacement in a first axial direction along said linear ion trap; or
   (ii) to apply one or more transient DC voltages or one or more transient DC voltage waveforms to at least some second electrodes in order to urge at least some ions having a second different radial displacement in a second axial direction along said linear ion trap, said second axial direction being different from said first axial direction.

6. A linear ion trap comprising:
   a plurality of longitudinally extending, stacked electrodes;
   a device arranged and adapted to apply an asymmetric voltage waveform to one or more of said electrodes so that, in use, ions become radially separated in a first radial direction according to their differential ion mobility and wherein in a mode of operation ions are ejected from or emerge from said linear ion trap in the first radial direction according to their differential ion mobility;
   a device arranged and adapted to apply a symmetric RF voltage to one or more of said electrodes so that, in use, ions are confined within said ion trap in a second radial direction by a RF pseudo-potential field; and
   wherein said linear ion trap is operated or maintained, in use, at a pressure <100 mbar.

7. A linear ion trap as claimed in claim 6, wherein said second radial direction is orthogonal to said first radial direction.

8. A linear ion trap as claimed in claim 1, further comprising a device arranged and adapted to maintain a substantially DC electric field in said first radial direction, wherein said DC electric field acts to retain at least some ions within said ion trap.

9. A linear ion trap as claimed in claim 1, wherein said linear ion trap comprises one or more upper planar electrodes, one or more lower planar electrodes and a plurality of intermediate planar electrodes arranged between said one or more upper planar electrodes and said one or more lower planar electrodes.

10. A linear ion trap as claimed in claim 9, wherein:
   (i) said one or more upper electrodes comprises a plurality of axially segmented upper electrode segments; or
   (ii) said one or more intermediate electrodes comprises a plurality of axially segmented intermediate electrode segments; or
   (iii) said one or more lower electrodes comprises a plurality of axially segmented lower electrode segments.

11. A linear ion trap as claimed in claim 1, wherein in a first mode of operation said ion trap is operated as a differential ion mobility separator so that ions emerge from or are ejected from said differential ion mobility separator according to their differential ion mobility and wherein in a second mode of operation said ion trap is operated either as: (i) an ion guide arranged so as to transmit ions without substantially separating ions according to either their differential ion mobility or their ion mobility; (ii) a collision, fragmentation or reaction device; or (iii) a device for separating ions according to their ion mobility.

12. A linear ion trap as claimed in claim 1, further comprising a device arranged and adapted to increase, step, scan, or decrease an amplitude or time period of said asymmetric voltage waveform applied to said one or more electrodes in order to increase, decrease or vary the radial separation or displacement of ions within said linear ion trap.

13. A linear ion trap as claimed in claim 1, further comprising:
   one or more entrance electrodes wherein, in use, a DC or RF potential is applied to one or more of said entrance electrodes in order to confine at least some ions axially within said linear ion trap in a mode of operation; or
   one or more exit electrodes wherein, in use, a DC or RF potential is applied to one or more of said exit electrodes in order to confine at least some ions axially within said linear ion trap in a mode of operation.

14. A differential ion mobility separator comprising a linear ion trap as claimed in claim 6.

15. A mass spectrometer comprising a differential ion mobility separator as claimed in claim 14.

16. A method of separating ions with
   a linear ion trap comprising a plurality of longitudinally extending, stacked electrodes, said method comprising:
   applying an asymmetric voltage waveform to one or more of said electrodes so that ions become radially separated according to their differential ion mobility;
   forming a DC axial potential barrier at a position along the axial length of said linear ion trap so that ions having a first differential ion mobility and a first radial displacement are retained axially within said linear ion trap by said axial potential barrier whereas ions having a second different differential ion mobility and a second different radial displacement emerge axially or are ejected axially from said linear ion trap when a force acting on the ions having the second different differential ion mobility in the axial direction is sufficient to overcome the DC axial potential barrier applied to exit electrodes; and
   operating or maintaining said linear ion trap at a pressure <100 mbar.

17. A method of separating ions with
   a linear ion trap comprising a plurality of longitudinally extending, stacked planar electrodes, said method comprising:
   applying an asymmetric voltage waveform to one or more of said electrodes so that ions become radially separated in a first radial direction according to their differential ion mobility and are ejected from or emerge from said linear ion trap in the first radial direction according to their differential ion mobility;
   applying a symmetric RF voltage to one or more of said electrodes so that ions are confined within said ion trap in a second radial direction by a RF pseudo-potential field; and
   operating or maintaining said linear ion trap at a pressure <100 mbar.

* * * * *